United States Patent [19]
Florisson et al.

[11] Patent Number: 4,783,168
[45] Date of Patent: Nov. 8, 1988

[54] METHOD OF DETERMINING A PHYSICAL PROPERTY OF A MEDIUM

[75] Inventors: Onno Florisson, Leek; Geert E. H. Joosten, Roden, both of Netherlands

[73] Assignee: N.V. Netherlandse Gasunie, Groningen, Netherlands

[21] Appl. No.: 39,864

[22] Filed: Apr. 20, 1987

[30] Foreign Application Priority Data

Apr. 19, 1986 [NL] Netherlands .......................... 8600998

[51] Int. Cl.⁴ .............................................. G01J 3/44
[52] U.S. Cl. .................................................... 356/301
[58] Field of Search ..................... 356/301, 72

[56] References Cited

U.S. PATENT DOCUMENTS 3,950,101 4/1976 Dewey, Jr. ........................... 356/51

Primary Examiner—F. L. Evans
Attorney, Agent, or Firm—Cushman, Darby & Cushman

[57] ABSTRACT

Method of determining a physical property of a medium, especially natural gas, comprising a qualitative and a quantitative analysis in which the components and the specific gravity of the medium and the specific gravities and weight fractions of the components are determined and the property to be determined is calculated with a formula known per se, at least one weight fraction being determined by Raman spectrometry.

3 Claims, 1 Drawing Sheet

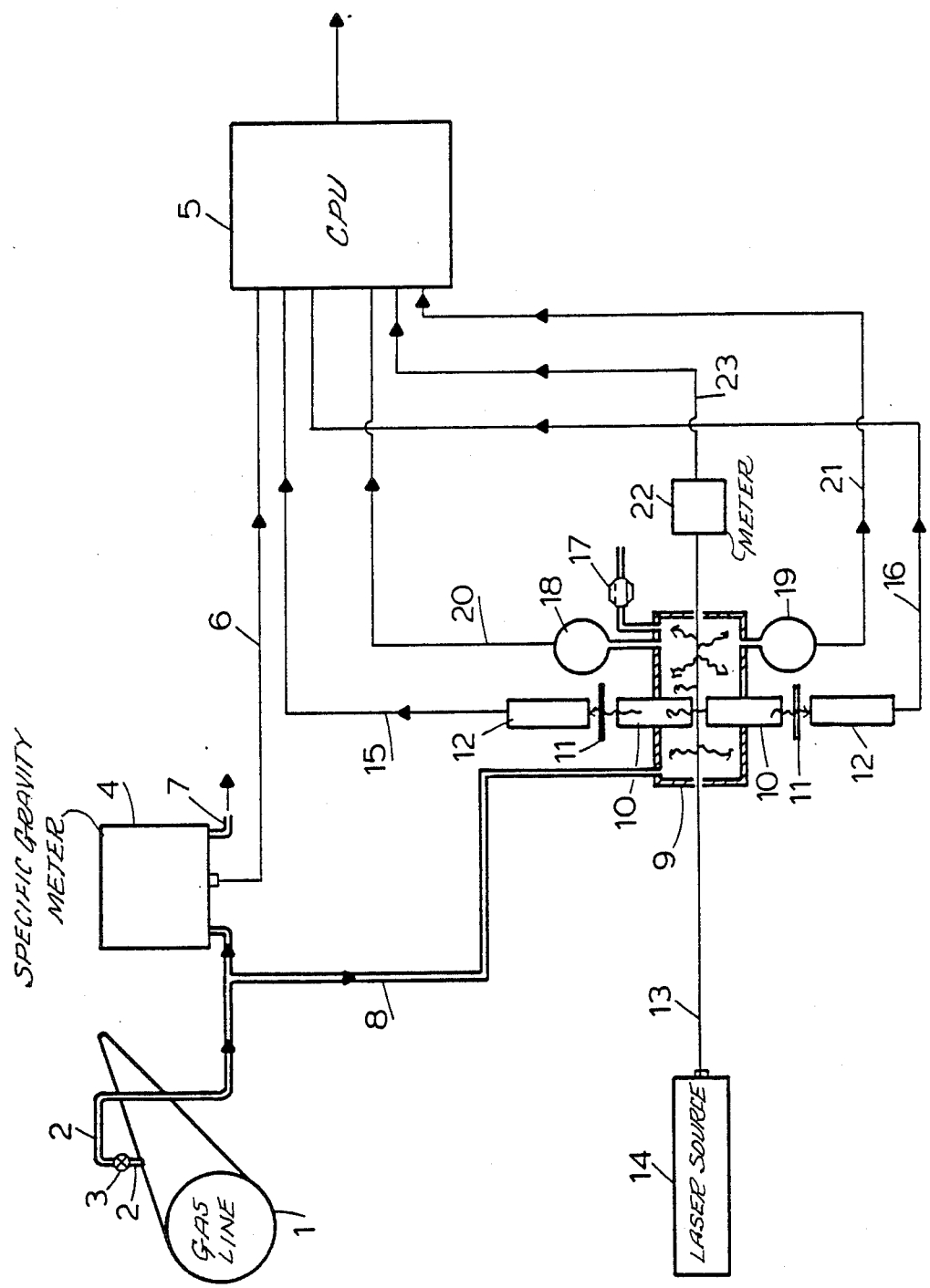

METHOD OF DETERMINING A PHYSICAL PROPERTY OF A MEDIUM

FIELD OF THE INVENTION

The invention relates to a method of determining a physical property of a medium comprising a qualitative and a quantitative analysis in which the components and the specific gravity of the medium and the specific gravities and weight fractions of the components are determined and the property to be determined is calculated using a formula.

The term 'component' shall here be understood to include a 'set of related components'. This is a set of components for which there is an (approximately) linear relationship between the calorific values and the specific gravities of the components. An example are the lower alkanes.

More in particular, the invention relates to a process for determination of the gross calorific value and/or the Wobbe index, a quantity in combustion engineering derived from it, of a combustible gas or liquid or a mixture thereof, the algebraic relationship between the calorific value and the concentration of the components being known.

BACKGROUND OF THE INVENTION

When combustible gases of different origin are mixed, it is of great technical and economic importance to be able to determine the calorific value and/or the Wobbe index of the mixture quickly, simply and cheaply.

The Wobbe index is defined by the expression $$W = \frac{H}{\sqrt{d}}$$

where

H = the gross calorific value of the gas, in MJ per m$^3$
d = the relative density of the gas with respect to air.

The Wobbe index is an important quantity in combustion engineering; when, at one and the same pressure, fuel gases of different composition but with the same Wobbe index are fed to gas-fired equipment, the heat produced is the same. When e.g. in an industrial plant a mixture of gases of different origin is used as fuel, stable operation requires that the gases be mixed in such a ratio, possibly with admixing of inert gas (in this connection, air may also be considered an inert gas), that a gas with a virtually constant Wobbe index is obtained.

From NL-A-7808476 it is known that when gases of different composition and different Wobbe index are burnt with equal quantities of air, the oxygen content of the flue gases can be directly correlated to the Wobbe index. This means that for measurement and control purposes it is not necessary to measure the Wobbe index as such, but it suffices to measure the oxygen content of said flue gases.

With the known method the Wobbe index or calorific value of a gas mixture can be determined within 30–60 seconds. However, in certain situations a quicker response of the measurement may be desirable. With the known (combustion) measuring method, this is impossible.

The object of the invention is, among other things, to provide a method of determining the gross calorific value of a combustible medium in which within a very short time, e.g. not more than 30 seconds, a virtually complete response of the measurement is obtained.

SUMMARY OF THE INVENTION

The method according to the invention is characterized in that at least one weight fraction is determined by Raman spectrometry.

With the method of the invention, a very fast (within 30 seconds), virtually complete response of the measurement is obtained. Another indication of the speed of the measurement is that within one time the time constant 63% of the response is obtained.

The method of the invention is in general applicable to a combination of phases. Under practical conditions it is to be preferred, in the case of a combination of phases, to determine the property to be determined for each individual phase.

BRIEF DESCRIPTION OF THE DRAWINGS

FIG. 1 is a schematic representation of apparatus to accomplish the method of the present invention.

DETAILED DESCRIPTION OF THE PREFERRED EMBODIMENT

By way of example, two groups of applications of the method according to the invention will be indicated in detail:

Group 1: all specific gravities and all minus 2 weight fractions of the components of the medium are known;

Group 2: all specific gravities except one and all weight fractions of the medium except one are known.

Group 1

Assume a homogeneous medium with

| (sets of related) components | i | $0 \leq i \leq n$ |
|---|---|---|
| weight fraction | $C_i$ | |
| specific gravity | $\rho_i$ | [kg/m$^3$] |
| calorific value i | $H_i$ | [MJ/kg] |
| specific gravity of medium | $\rho$ | [kg/m$^3$] |
| calorific value of medium | $H$ | [MJ/kg] |

Suppose that $\rho$, $\rho_i$, $H_i$ are known, $C_i=0$; $C_i=1$; $C_o$, $C_1$, H are unknown
Then H can be calculated with:

$$H = \sum_{i=0}^{n} C_i H_i$$

where (hereinafter referred to as 1)

$$C_i = \left( \rho - \rho_o + \sum_{i=2}^{n} C_i \rho_o - \sum_{i=2}^{n} C_i \rho_i \right) / (\rho_i - \rho_o)$$

and (hereinafter referred to as 2)

$$C_o = 1 - \sum_{i=1}^{n} C_i$$

(hereinafter referred to as 3)

Group 2

Assume a homogeneous medium with (sets of related) components

| i | $0 \leq i \leq n$ | |
|---|---|---|
| weight fraction | $C_i$ | |
| specific gravity | $\rho_i$ | [kg/m³] |
| calorific value i | $H_i$ | [MJ/kg] |
| specific gravity of medium | $\rho$ | [kg/m³] |
| calorific value of medium | $H$ | [MJ/kg] |

Suppose that $\rho$, $\rho i = 0$, $H_i 0\,(\rho_i)$, $C_i = 0$ are known; $\rho 0$, $C_o$, $H_o$, $(\rho_o)$, $H$ are unknown.

H can be calculated with $$H = \sum_{i=0}^{n} C_i H_i (\rho_i),$$

(hereinafter referred to as (5)) where $$\rho_o = \left(\rho - \sum_{i=1}^{n} C_i \rho_i\right) / \left(1 - \sum_{i=1}^{n} C_i\right)$$

(hereinafter referred to as (6)) and $$C_o = 1 - \sum_{i=1}^{n} C_i$$

(hereinafter referred to as (8))

For application to a homogeneous gas,
1. the mass fractions must be replaced by volume fractions;
2. the specific gravities in the formulas (2) and (6) must be replaced by the reciprocal densities relative to air, and in the formulas (1), (3), (5), and (8) by the density relative to air;
3. the calorific values [MJ/kg] must be replaced by the calorific values [MJ/$m_o^3$].

The formulas remain the same, except that the constants in them have to be adjusted.

With the method according to the invention the calorific value of a gaseous and/or liquid medium can be determined continuously, which is advantageous in the case of gas mixtures whose composition can change greatly within a short period. This can be the case e.g. in the chamical industry, where flue gases and/or residual gases are sometimes utilized as fuel gas for combustion installations.

Another advantage of the process according to the invention is that it is intrinsically safe when applied in an installation. This means that such an installation can under no conditions function as a (potential) ignition source for a combustion gas which is (unintentionally) present.

The method according to the invention can also be applied for the determination of other properties of gases or liquids, e.g. determination of the dewpoint or phase transition in general and compressibility.

EXAMPLE

Natural gas, of which only the main components are considered.

Take for
i=0 the set of related alkanes
i=1 the nitrogen
i=2 the carbon monoxide
Assume the following are known:
the volume concentration of nitrogen $C_1 = 0.1268$;
the volume concentration of carbon dioxide $C_2 = 0.0198$;
the density of the natural gas relative to air $d = 0.6529$;
$C_1$ and $C_2$ are determined by Raman spectrometry.

The density of nitrogen relative to air is $d_1 = 0.967$;
the density of carbon dioxide relative to air is $d_2 = 1.530$;
the density of the set of related alkanes relative to air is $d_o = 0.586$;
the calorific value of the set of related alkanes is $H_o = 5.67 + 61.37\,d_o$ (MJ/$m_o^3$);
the calorific values of nitrogen and carbon dioxide are $H_1$ and $H_2$, respectively, and are both zero.

From (8) we calculate $C_o = 0.853$ and, with (6), $d_o = 0.586$. Substitution of all these values in (5) yields, with $H_o = 41.63$ [MJ/$m_o^3$], $H = 35.5$ [MJ/$m_o^3$], which agrees exactly with a calculation based on a gas chromatographic analysis of the natural gas.

The method according to the invention will now be explained with reference to a figure. In the figure, a functional diagram is indicated of a measuring system in which the method according to the invention is used for determination of the gross calorific value of a natural gas. The carbon dioxide and nitrogen concentrations are both determined by Raman spectrometry.

By 1 a natural gas transport line is indicated, to which a sampling line 2 is connected. Line 2 can be closed with valve 3. When valve 3 is open, natural gas flows to a device 4 in which the specific gravity of the natural gas is determined. The measured value is fed to the data processing unit 5 via signal line 6. Line 7 is a discharge line of device 4, through which the samples natural gas is discharged. In addition, natural gas flows through line 8 to a cuvette 9, in which, with the aid of light transmitters 10, optical filters 11 and sensors 12 the light scattering of laser beam 13 generated in laser source 14 is measured to be fed to the central processing unit 5 via signal lines 15 and 16. The intensity at a particular wavelength in the scattered light is a measure of the concentration of a particular component or set of related components in the medium. This measuring method is known per se as Raman spectrometry. With device 17 the pressure in cuvette 9 is controlled at a particular level. The pressure and temperature in cuvette 9 are measured with sensors 18 and 19, respectively, and are fed to the central processing unit 5 via signal lines 20 and 21.

The power of laser source 14 is measured with meter 22 and fed to the central processing unit 5 via signal line..

In the central processing unit 5 the calorific value of the medium is numerically calculated with the formulas and calibration data already given (constants and standardization factors).

We claim:
1. Method of determining the calorific value of a medium, comprising the steps of:
   determining the specific gravity of the medium;
   measuring the respective concentrations of various components and determining their identity within the medium using Raman spectrometry,
   calculating the calorific value of the medium according to the equation

$$H = \sum_{i=0}^{n} C_i H_i(P_i)$$

wherein H is the calorific value of the medium in MJ/m$^3$, $C_i$ is the weight fraction of a particular component in %, $H_i$ is the calorific value of a particular component in MJ/kg, $p_i$ is the specific gravity of a particular component in Kg/m$^3$, and n is the number of components.

2. Method according to claim 1, characterized in that the gross calorific value of the medium is determined.

3. Method according to claim 2, characterized in that the gross calorific value of each individual phase of which the medium is composed is determined.

* * * * *